United States Patent [19]
Herrmann et al.

[11] Patent Number: 5,726,333
[45] Date of Patent: Mar. 10, 1998

[54] ORGANOMETALLIC COMPOUND

[75] Inventors: Hans-Friedrich Herrmann, Gross-Gerau; Frank Küber, Oberursel; Michael Aulbach, Hofheim; Wolfgang Anton Herrmann, Freising; Marc Morawietz, München, all of Germany

[73] Assignee: Hoechst AG, Germany

[21] Appl. No.: 499,854

[22] Filed: Jul. 10, 1995

[30] Foreign Application Priority Data

Jul. 9, 1994 [DE] Germany ............... 44 24 227.1

[51] Int. Cl.$^6$ ............... C07F 17/00; C07F 7/00
[52] U.S. Cl. ............... 556/11; 556/12; 556/28; 556/43; 556/53; 556/56; 526/160; 526/943; 502/103; 502/117; 502/158
[58] Field of Search ............... 556/11, 12, 28, 556/43, 53, 56; 526/943, 160; 502/103, 117, 158

[56] References Cited

FOREIGN PATENT DOCUMENTS 2024333  3/1991  Canada.

OTHER PUBLICATIONS

Borhme et al., J. Organomet. Chem., vol. 472, No. 1-2, pp. 39–41, Jun. 14, 1994.
R. Halterman, "Synthesis and Applications . . . ", Chem. Rev. 1992, vol. 92, 965–994.
A. Hughes et al., "Efficient New Synthetic . . . ", Organometallics, 1993, vol. 12, 1936–1945.

*Primary Examiner*—Porfirio Nazario-Gonzalez
*Attorney, Agent, or Firm*—Connolly & Hutz

[57] ABSTRACT

The invention relates to an organometallic compound of the formula I,

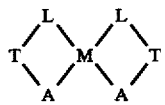

where M is a tetravalent metal, L are, independently of one another, identical or different and are each a $\pi$ ligand, T are, independently of one another, identical or different and are each a bridge and A are, independently of one another, identical or different and are each a $\pi$ ligand or another electron donor.

21 Claims, No Drawings

ORGANOMETALLIC COMPOUND

The present invention relates to an organometallic compound which can be very advantageously used as a catalyst component, for example for the preparation of polyolefins.

Metallocene compounds of transition group IV are, in combination with methylaluminoxane (MAO), active catalysts for the polymerization of olefins. The preparation of polyolefins using soluble metallocene compounds in combination with aluminoxanes or other cocatalysts which, owing to their Lewis acidity, can convert the neutral metallocene into a cation and stabilize it, is known from the literature.

Metallocenes and semisandwich complexes are not only of great interest with regard to the polymerization or oligomerization of olefins. They can also be used as hydrogenation, epoxidation, isomerization and C—C coupling catalysts (Chem. Rev. 1992, 92, 965–994).

Metallocenes in which a π ligand has been replaced by a heteroatom (e.g. N, O or P) are known (cf. EP 416 815). The preparation of the compounds described there proves to be difficult and proceeds only in moderate yields.

From the literature it is known that Cp(H)CH$_2$CH$_2$CH$_2$N(CH$_3$)H can be reacted with zirconium or hafnium dimethyltetramide directly and without addition of a base to give complexes of the types described in EP 416 815 (Organometallics, 1993, 12, 1936).

It is thus an object of the invention to find an organometallic compound which avoids the disadvantages of the prior art.

It has surprisingly been found that reaction of a metal tetramide with a ligand system without addition of a base such as butyllithium directly gives a metallocene.

The present invention accordingly provides an organometallic compound of the formula I,

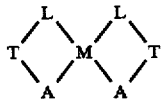

(I)

where M is a tetravalent metal, L are, independently of one another, identical or different and are each a π ligand, T are, independently of one another, identical or different and are each a bridge and A are, independently of one another, identical or different and are each a π ligand or another electron donor.

Preferably, M is titanium, zirconium, hafnium, vanadium, niobium, tantalum, scandium, yttrium or a rare earth metal, particularly preferably titanium or zirconium. L are preferably identical and a substituted or unsubstituted cyclopentadienyl group. T are preferably identical and are [R$^1_2$B]$_n$, where B is carbon, silicon or germanium, the radicals R$^1$ are identical or different and are each hydrogen or a C$_1$–C$_{30}$-hydrocarbon radical such as C$_1$–C$_{10}$-alkyl or C$_6$–C$_{14}$-aryl, and n is equal to 1, 2, 3 or 4. A are preferably identical and a π ligand such as a substituted or unsubstituted cyclopentadienyl group or an electron donor such as O, PR$^2$, S or NR$^2$, where R$^2$ is hydrogen or a C$_1$–C$_{30}$-hydrocarbon radical such as C$_1$–C$_{10}$-alkyl or C$_6$–C$_{14}$-aryl.

Examples of substituted cyclopentadienyl groups are: tetramethylcyclopentadienyl, methylcyclopentadienyl, methyl-tert-butylcyclopentadienyl, tert-butylcyclopentadienyl, isopropylcyclopentadienyl, dimethylcyclopentadienyl, trimethylcyclopentadienyl, trimethylethylcyclopentadienyl, phenylcyclopentadienyl, diphenylcyclopentadienyl, indenyl, 2-methylindenyl, 2-ethylindenyl, 3-methylindenyl, 3-tert-butylindenyl, 3-trimethylsilylindenyl, 2-methyl-4-phenylindenyl, 2-ethyl-4-phenyl-indenyl, 2-methyl-4-naphthylindenyl, 2-methyl-4-isopropylindenyl, benzoindenyl, 2-methyl-4,5-benzoindenyl, 2-methyl-α-acenaphthindenyl, 2-methyl-4,6-diisopropylindenyl, fluorenyl, 4-methylfluorenyl or 2,7-di-tert-butylfluorenyl.

Examples of preferred bridges T are: dimethylsilanediyl, methylphenylsilanediyl, diphenylsilanediyl, dimethylgermandiyl, 1,2-tetramethyldisilanediyl, 1,2-ethylidene, 1,2-propylidene, 1,2-butylidene, 1,3-propylidene, 1,4-butylidene.

Examples of preferred structural elements A are: cyclopentadienyl, or substituted cyclopentadienyl groups such as indenyl, fluorenyl, tetramethylcyclopentadienyl, methylcyclopentadienyl, methyl-tert-butylcyclopentadienyl, tert-butylcyclopentadienyl, isopropylcyclopenta-dienyl, dimethylcyclopentadienyl, trimethylcyclopentadienyl, trimethylethylcyclopentadienyl, phenylcyclopentadienyl, diphenylcyclopentadienyl, indenyl, 2-methylindenyl, 2-ethylindenyl, 3-methylindenyl, 3-tert-butylindenyl, 3-trimethylsilylindenyl, 2-methyl-4-phenylindenyl, 2-ethyl-4-phenylindenyl, 2-methyl-4-naphthylindenyl, 2-methyl-4-isopropylindenyl, benzoindenyl, 2-methyl-4,5-benzoindenyl, 2-methyl-α-acenaphthindenyl, 2-methyl-4,6-diisopropylindenyl, fluorenyl, 4-methylfluorenyl or 2,7-di-tert-butylfluorenyl or electron donors such as tert-butylamido, cyclohexylamido, phenylamido, 2,6-diisopropylphenylamido, 2,6-di-tert-butylphenylamido, cyclododecylamido or —O.

Examples of particularly preferred compounds of the formula I are:

bis{[(tert-butylamido)dimethylsilyl)]cyclopentadienyl}zirconium, bis{[(tert-butylamido)dimethylsilyl)]cyclopentadienyl}hafnium, bis{[(tert-butylamido)diphenylsilyl)]cyclopentadienyl}zirconium, bis{[(tert-butylamido)phenylmethylsilyl)]cyclopentadienyl}zirconium, bis{[(tert-butylamido)ethylidene)]cyclopentadienyl}zirconium, bis{[(tert-butylamido)isopropylidene)]cyclopentadienyl}zirconium, bis{[(tert-butylamido)dimethylsilyl)]tetramethylcyclopenta-dienyl}zirconium, bis{[(tert-butylamido)dimethylsilyl)]methylcyclopentadienyl}zirconium, bis{[(2,6-diisopropylanilido)dimethylsilyl)]methylcyclopenta-dienyl}zirconium, bis{[(tert-butylamido)dimethylsilyl)]tert-butylcyclopenta-dienyl}zirconium, bis{[(tert-butylamido)dimethylsilyl)]indenyl}zirconium, bis{[(tert-butylamido)dimethylsilyl)]2-methylindenyl}zirconium, bis{[(tert-butylamido)dimethylsilyl)]2-methyl-4-phenylindenyl}zirconium, bis{[(tert-butylamido)dimethylsilyl)]2-methyl-4,5-benzoindenyl}zirconium, bis{[(tert-butylsmido)dimethylsilyl)]2-methyl-4,6-diisopropylindenyl}zirconium, bis{[(tert-butylsmido)dimethylsilyl)]fluorenyl}zirconium, bis{[(phenylamido)dimethylsilyl)]cyclopentadienyl}zirconium, bis{[(phenylamido)dimethylsilyl)]cyclopentadienyl}hafnium, bis{[(phenylamido)diphenylsilyl)]cyclopentadienyl}zirconium, bis{[(phenylamido)phenylmethylsilyl)]cyclopentadienyl}zirconium, bis{[(phenylamido)ethylidene)]cyclopentadienyl}zirconium, bis{[(phenylamido)isopropylidene)]cyclopentadienyl}zirconium, bis{[(phenylamido)dimethylsilyl)]tetramethylcyclopentadienyl}zirconium, bis{[(phenylamido)dimethylsilyl)]methylcyclopentadienyl}zirconium, bis{[(2,6-diisopropylanilido)dimethylsilyl)]methylcyclopentadienyl}zirconium, bis{[(phenylamido)dimethylsilyl)]tert-butylcyclopentadienyl}zirconium, bis{[(phenylamido)dimethylsilyl)]indenyl}zirconium, bis{[(phenylamido)dimethylsilyl)]2-methylindenyl}zirconium, bis{[(phenylamido)dimethylsilyl)]2-methyl-4-phenylindenyl}zirconium, bis{[(phenylamido)dimethylsilyl)]2-methyl-4,5-benzoindenyl}zirconium, bis{[(phenylamido)dimethylsilyl)]2-methyl-4,6-diisopropylindenyl}zirconium, bis{[(phenylamido)dimethylsilyl)]fluorenyl}zirconium, bis{[(2,6-diisopropylanilido)dimethylsilyl)]indenyl}zirconium, bis{[(2,6-diisopropylanilido)dimethylsilyl)]tert-butylcyclopentadienyl}zirconium, bis{[(2,6-di-tert-butylanilido)dimethylsiyl)]methylcyclopentadienyl}zirconium, bis{[(2,6-di-tert-butylanilido)dimethylsilyl)]indenyl}zirconium, bis(dimethylamido){[(cyclohexylanilido>dimethylsilyl)]-methylcyclopentadienyl}zirconium, bis{[(cyclohexylamido)dimethylsilyl)]indenyl}zirconium.

The present invention further provides a process for preparing a compound of the formula I, which comprises reacting a compound of the formula II where L is a π ligand, T is a bridge and A is a π ligand or another electron donor, with a compound of the formula III, where M is a tetravalent metal and $R^3$ is a $C_1$–$C_{20}$-alkyl radical such as methyl, ethyl or isobutyl.

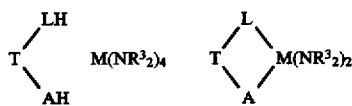

The reaction is preferably carried out in an aprotic solvent, for example toluene or hexane. The temperature can be between −78° and 140° C., preferably from 0° to 110° C. The compound of the formula II can be used in excess, preference is given to using 2–3 equivalents of the compound of the formula II based on the metal tetramide of the formula III. If a metal tetramide of the formula III is first reacted with one equivalent of a compound of the formula II, there is obtained a compound of the formula IV, where L is π ligand, T is a bridge, A is a π ligand or another electron donor, M is a tetravalent metal and $R^3$ is a $C_1$–$C_{20}$-alkyl radical such as methyl, ethyl or isobutyl (such compounds are described, for example in EP 416 815). If the compound of the formula IV is, after isolation and purification, reacted with one further equivalent of the compound of the formula II originally used, there are obtained compounds of the formula I in which the two structural elements -L-T-A- are identical. If the compound of the formula IV is reacted with a compound of the formula II which is different from the compound of the formula II originally used, there are obtained compounds of the formula I in which the two structural elements -L-T-A- are different from one another. The reaction can also be carried out in situ.

The processes for preparing compounds of the formula II are known (Chem. Ber. 1990, 123, 1649–1651). The processes for preparing compounds of the formula III are likewise known (J. Chem. Soc. 1960, 3857–3861).

Compounds of the formula I are, in combination with a cocatalyst, suitable catalysts for the polymerization of olefins to produce olefin polymers.

The present invention accordingly also provides a process for preparing an olefin polymer by polymerization or copolymerization of at least one olefin in the presence of a catalyst, wherein the catalyst comprises at least one compound of the formula I and at least one cocatalyst.

Preferably, olefins of the formula $R^aCH=CH-R^b$, where $R^a$ and $R^b$ are identical or different and are each a hydrogen atom or a saturated or unsaturated hydrocarbon radical having from 1 to 20 carbon atoms, in particular from 1 to 10 carbon atoms, or $R^a$ and $R^b$ can form one or more rings together with the atoms connecting them, are polymerized or copolymerized with other olefins of the abovementioned type. Examples of olefins of the abovementioned formula are ethylene, propylene, 1-butene, butadiene, 1-hexene, 4-methyl-1-pentene, 1-octene, norbornene, norbornadiene or styrene. Preference is given to polymerizing ethylene and propylene.

The polymerization or copolymerization is preferably carried out at a temperature of from −60° to 200° C., preferably between 50° and 150° C. The pressure is between 0.5 and 100 bar, preferably between 5 and 64 bar. The polymerization can be carried out continuously or batchwise, in one or more stages, in solution, suspension, bulk or in the gas phase. If necessary, hydrogen can be added as molecular weight regulator and/or to increase the activity.

The catalyst preferably comprises one compound of the formula I and one cocatalyst. It is also possible to use mixtures of the compounds of the invention, for example with other metallocenes or classical Ziegler-Natta catalysts. This enables polyolefins having a broad or multimodal molecular weight distribution to be obtained.

The cocatalyst used in the process of the invention is preferably an aluminoxane which preferably has the formula V or VI.

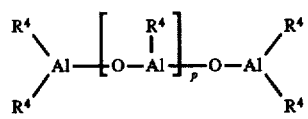

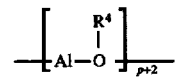

In these formulae, the radicals $R^4$ can be identical or different and each can be a hydrocarbon radical having from 1 to 20 carbon atoms, preferably from 1 to 10 carbon atoms, or hydrogen, and p is an integer from 2 to 50, preferably from 10 to 35. Particularly preferably, the radicals $R^4$ are identical and are methyl, isobutyl, phenyl or benzyl, particularly preferably methyl. If the radicals $R^4$ are different, they are preferably methyl and hydrogen or methyl and isobutyl, with hydrogen preferably being present in a proportion by number of from 0.01 to 40% (of the radicals $R^4$). The processes for preparing the aluminoxanes are known (EP 372 483).

The exact three-dimensional structure of the aluminoxanes is not known. For example, it is conceivable that chains and rings are connected to form larger two-dimensional and three-dimensional structures (cf. J. Am. Chem. Soc. 1993, 115, 4971).

It is possible to preactivate the metal compound prior to use in the polymerization reaction using a cocatalyst, e.g. an aluminoxane. This can increase the polymerization activity and improve the particle morphology of the polymer obtained. The preactivation is carried out in solution. The metal compound is preferably dissolved in a solution of the aluminoxane in an inert solvent. Suitable solvents are, in particular, aliphatic and aromatic hydrocarbons. Particular preference is given to using toluene.

The concentration of the aluminoxane in solution is in a range from about 1% by weight to saturation, preferably from 5 to 30% by weight based on the total amount of solvent. The metallocene can be used in the same concentration, but it is preferably used in an amount of from $10^{-4}$ to 1 mol per mol of aluminoxane. The time for the preactivation is between 5 minutes and 60 hours, preferably from 5 to 60 minutes. It is carried out at a temperature between $-78°$ and $100°$ C., preferably from $0°$ to $70°$ C.

A prepolymerization can be carried out by means of the metal compound. For the prepolymerization, preference is given to using the (or one of the) olefin(s) used in the polymerization.

To control the particle morphology, the metal compound can also be applied to a support. Suitable support materials are, for example, silica gels, aluminum oxides, solid aluminoxane or other inorganic support materials such as, for example, magnesium chloride. A polyolefin powder in finely divided form is also a suitable support material.

In the polymerization process of the invention, use can be made as suitable cocatalysts of compounds of the formulae $R^5_xNH_{4-x}BR^6_4$, $R^5_xPH_{4-x}BR^6_4$, $R^5_3CBR^6_4$ or $BR^6_3$ in place of or in addition to an aluminoxane. In these formulae, x is an integer from 1 to 4, preferably 3, the radicals $R^5$ are identical or different, preferably identical, and are each a saturated or unsaturated hydrocarbon radical having from 1 to 20, preferably from 1 to 10, carbon atoms. Two radicals $R^5$ can also form a saturated or unsaturated ring together with the atoms connecting them. The radicals $R^6$ are identical or different and are each an aromatic hydrocarbon radical having from 6 to 20, preferably from 6 to 10, carbon atoms, which radical may be substituted by fluorine. In particular, $R^5$ is ethyl, propyl, butyl or phenyl and $R^6$ is phenyl, pentafluorophenyl, 3,5-bistrifluoromethylphenyl, mesityl, xylyl or tolyl (cf. EP 277 003, EP 277 004 and EP 426 638). In use of these cocatalysts, the polymerization catalyst comprises the reaction product of the compound of the formula I and one of the compounds specified. Therefore, this reaction product is first prepared in a separate step, preferably outside the polymerization reactor. In principle, a suitable cocatalyst is any compound which, owing to its Lewis acidity, can convert the neutral metal compound into a cation and stabilize the latter. The metallocene is here preferably used in a concentration, based on the transition metal, of from $10^{-3}$ to $10^{-8}$, preferably from $10^{-4}$ to $10^{-7}$, mol of transition metal per dm$^3$ of solvent or dm$^3$ of reactor volume. The aluminoxane is used in a concentration of from $10^{-5}$ to $10^{-1}$ mol, preferably from $10^{-4}$ to $10^{-2}$ mol, per dm$^3$ of solvent or dm$^3$ of reactor volume. The other cocatalysts are used in approximately equimolar amounts to the transition metal compound. However, it is also possible in principle to use higher concentrations.

To remove catalyst poisons present in the olefin, purification using an aluminum alkyl, preferably trimethylaluminum or triethylaluminum is advantageous. This purification can be carried out in the polymerization system itself or the olefin is, prior to addition, brought into contact with the aluminum compound and subsequently separated again.

If the polymerization is carried out as suspension or solution polymerization, use is made of an inert solvent customary for the Ziegler low-pressure process. For example, the polymerization is carried out in an aliphatic or cycloaliphatic hydrocarbon; examples of such hydrocarbons which may be mentioned are propane, butane, hexane, heptane, isooctane, cyclohexane, methylcyclohexane. Furthermore, use can be made of a petroleum or hydrogenated diesel oil fraction. It is also possible to use toluene. If inert solvents are used, the monomers are metered in liquid or gaseous form. The polymerization time can be of any desired length, since the catalyst system to be used according to the invention shows only a small time-dependent fall in the polymerization activity.

The polyolefins prepared according to the process described have particular importance for the production of waxes or shaped bodies such as, for example, films, plates or large hollow bodies.

The following examples are to illustrate the invention:

All glass apparatus was baked out in vacuo and flushed with argon. All operations were carried out with exclusion of moisture and oxygen in Schlenk vessels. The solvents used were distilled under argon from an Na/K alloy. Toluene-soluble methylaluminoxane was used for the polymerization examples as a 10% strength by weight toluene solution having a mean degree of oligomerization of n=20 (Witco). According to aluminum analysis, the content is 36 mg of Al/ml.

Definitions:

| | | |
|---|---|---|
| VN | = | viscosity number |
| $M_w$ | = | weight-average molecular weight (determined by gel permeation chromatography) |
| $M_w/M_n$ | = | molecular weight dispersity |

1. Bis{[(phenylamido)dimethylsilyl]cyclopentadienyl}zirconium 1:

A 100 ml flask fitted with reflux condenser is charged at $-78°$ C. with 0.379 g (1 mmol) of Zr(NEt$_2$)$_4$ in 20 ml of toluene. 0.430 g (2 mmol) of Me$_2$Si(C$_5$H$_5$)(NHPh) in 10 ml of toluene is then added dropwise by means of a syringe. The reaction mixture is warmed to room temperature. It is heated for a further 12 hours under reflux and the solvent is subsequently removed in vacuo (0.5 mbar). The product remains as a yellow-brown solid. The yield is 0.512 g (0.99 mmol, 99%). $^1$H-NMR (400 MHz, C$_6$D$_6$, 25° C.): 0.37, 0.45 (s, 6H, Si(CH$_3$)$_2$), 5.65, 5.89, 5.95, 6.17 (4 q, 8H, H-Cp), 6.89–7.20 (m, 10H, arom. H).

2. Bis{[dimethylsilylbiscyclopentadienyl}zirconium 2:

A 100 ml flask fitted with reflux condenser is charged at $-50°$ C. with 0.379 g (1 mmol) of Zr(NEt$_2$)$_4$ in 20 ml of toluene. 0.376 g (2 mmol) of Me$_2$Si(C$_5$H$_5$)$_2$ in 10 ml of toluene are added dropwise by means of a syringe. The reaction mixture is warmed to room temperature. It is heated for a further 12 hours under reflux and the solvent is subsequently removed in vacuo (0.5 mbar). The crude product is purified by sublimation (100° C./0.001 mbar). The yield is 0.420 g (0.90 mmol, 90%). $^1$H-NMR (400 MHz, C$_6$D$_6$, 25° C.): 0.37 (s, 12 H, SiCH$_3$), 5.70 (t, 4H, CpH), 5.86 (t, 4H, CpH).

3. Bis{[(phenylamido)dimethylsilyl]cyclopentadienyl}-hafnium 3:

A 100 ml flask fitted with reflux condenser is charged at $-78°$ C. with 0.47 g (1 mmol) of Hf(NEt$_2$)$_4$ in 20 ml of toluene. 0.43 g (2 mmol) of Me$_2$Si(C$_5$H$_5$)(NHPh) in 10 ml of toluene is added dropwise by means of a syringe. The reaction mixture is warmed to room temperature. It is heated for a further 12 hours under reflux and the solvent is subsequently removed in vacuo (0.5 mbar). The product remains as a yellow solid. The yield is 0.38 g (0.90 mmol; 90%). $^1$H-NMR (400 MHz, $C_6D_6$, 30° C.): 0.36, 0.45 (s, 12H, $Si(CH_3)_2$), 5.59 (q, 2H, CpH), 5.90 (t, 4H, CpH), 6.11 (q, 2H, CpH), 6.88–7.32, (m, 10H, arom. H).

Polymerization examples:

EXAMPLE 1

A dry 1.5 dm$^3$ stirred reactor is flushed with nitrogen to remove oxygen, charged with 0.9 dm$^3$ of an inert diesel oil (bp. 100°–120° C.) and heated to 80° C. In parallel thereto, 30 mg of compound 1 are dissolved in a 10% strength by weight solution of methylaluminoxane in toluene (12 mmol of Al) and preactivated by stirring. The polymerization is started by metering in the catalyst solution and pressurization with 7 bar of ethylene. After one hour at 80° C., the reactor is vented, the polymer is filtered from the suspension and is dried for 12 hours in a vacuum drying oven. This gives 11.9 g of PE powder corresponding to an activity of 26 g of PE/mmol of Zr/h/bar. The viscosity number is 300 cm$^3$/g. The molecular weight distribution according to GPC is $M_w/M_n$=2.7. The weight-average molecular weight is $M_w$=174,000 g/mol.

EXAMPLE 2

The polymerization of Example 1 was repeated except that 59 mg of compound 3 and 1500 mg of MAO (26 mmol of Al) were used. This gave 5.7 g of polyethylene powder corresponding to 100 g of PE/g of cat./h and having a viscosity number of 210 cm$^3$/g.

EXAMPLE 3

The polymerization of Example 1 was repeated except that 9.8 mg of compound 2 and 1500 mg of MAO (26 mmol of Al) were used. This gave 19.6 g of PE powder (activity= 1990 g of PE/g of cat./h; VN=135 cm$^3$/g).

EXAMPLE 4

The polymerization of Example 1 was repeated except that 8.1 mg of compound 2 and 1500 mg of MAO (26 mmol of Al) were used. The polymerization temperature was 70° C. This gave 6.6 g of PE powder (activity=810 g of PE/g of cat./h; VN=233 cm$^3$/g).

We claim:

1. An organometallic compound of the formula I,

 (I)

where M is a tetravalent metal, L are, independently of one another, identical or different and are each a substituted cyclopentadienyl group T are, independently of one another, identical or different and are each a bridge and A are independently of one another, identical or different and are each a π ligand or an electron donor.

2. The organometallic compound as claimed in claim 1, wherein L are identical or different and are each an unsubstituted or substituted cyclopentadienyl group.

3. The organometallic compound as claimed in claim 1, wherein A are identical or different and are each an unsubstituted or substituted cyclopentadienyl group.

4. The organometallic compound as claimed in claim 1, wherein T are identical or different and are each $[R^1_2B]_n$, where B is carbon, silicon or germanium and the radicals $R^1$ are identical or different and are each hydrogen or a $C_1$–$C_{30}$-hydro-carbon radical.

5. A catalyst component comprising at least one organometallic compound as claimed in claim 1 combined with at least one cocatalyst.

6. The catalyst component as claimed in claim 5, wherein the cocatalyst is an aluminoxane.

7. The catalyst component as claimed in claim 5, additionally comprising a support.

8. A process for preparing a compound of the formula I,

 (I)

where M is a tetravalent metal, L are, independently of one another, identical or different and are each a π ligand, T are, independently of one another, identical or different and are each a bridge and A are, independently of one another, identical or different and are each a π ligand or another electron donor, which comprises reacting a compound of the formula II,

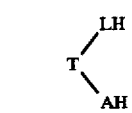

where L is a π ligand, T is a bridge and A is a π ligand or another electron donor, in excess with a compound of the formula III, $$M(NR^3_2)_4 \quad\quad III$$

where M is a tetravalent metal and $R^3$ is a $C_1$–$C_{20}$-alkyl radical.

9. The organometallic compound as claimed in claim 1, wherein M is titanium, zirconium, hafnium, vanadium, niobium, tantalum, scandium, yttrium or a rare earth metal, A are identical or different and each are an unsubstituted or substituted cyclopentadienyl group, and T are identical or different and are each $(r^1_2B)n$, where B is carbon, silicon or germanium and the radicals $R^1$ are identical or different and are each hydrogen or a $C_1$–$C_{30}$-hydro-carbon radical.

10. The organometallic compound as claimed in claim 9, wherein M is titanium or zirconium, all the L are identical, all the T are identical and all the A are identical.

11. The organometallic compound as claimed in claim 9, wherein L selected from the group consisting of cyclopentadienyl, tetramethylcyclopentadienyl, methylcyclopentadienyl, methyl-tert-butylcylclopentadienyl, tert-butylcyclo-pentadienyl, isopropycyclopentadienyl, dimethylcyclopentadienyl, trimethylcyclopentadienyl, trimethylethylcyclopentadienyl, phenylcyclopentadienyl, diphenylcyclopentadienyl, indenyl, 2-methylindenyl, 2-ethylindenyl, 3-methylindenyl, 3-tert-butylindenyl, 3-trimethylsilylindenyl, 2-methyl-4-phenylindenyl, 2-ethyl-4-penylindenyl, 2-methyl-4-naphthylindenyl, 2-methyl-4-isopropylindenyl, benzoindenyl, 2-methyl-4,5-benzoindenyl, 2-methyl-α-acenaphthindenyl, 2-methyl-4,6-diisopropylindenyl, fluorenyl, 4-methylfluorenyl and 2,7-di-tert-butylfluorenyl.

12. The organometallic compound as claimed in claim 1, wherein T is selected from the group consisting of dimethylsilanediyl, methylphenylsilanediyl, diphenylsilanediyl, dimethylgermandiyl, 1,2-tetramethyldisilanediyl, 1,2-ethylidene, 1,2-propylidene, 1,2-butylidene, 1,3-propylidene and 1,4-butylidene.

13. The organometallic compound as claimed in claim 1, wherein A is selected from the group consisting of cyclopentadienyl, tetramethylcyclopentadienyl, methylcyclopentadienyl, methyl-tert-butylcyclopentadienyl, methylcyclopentadienyl, methyl-tert-butylcyclopentadienyl, tert-butylcyclopentadienyl, isopropylcyclopentadientyl, dimethylcyclopentadienyl, trimethylcyclopentadienyl, trimethylethylcyclopentadienyl, phenylcyclopentadienyl, diphenylcyclopentadienyl, indenyl, 2-methylindenyl, 2-ethylindenyl, 3-methylindenyl, 3-tert-butylindenyl, 3-trimethylsilylindenyl, 2-methyl-4-phenylindenyl, 2-ethyl-4-phenylindenyl, 2-methyl-4-naphthylindenyl, 2-methyl-4-isopropylindenyl, benzoindenyl, 2-methyl-4,5-benzoindenyl, 2-methyl-α-acenaphthindenyl, 2-methyl-4,6-diisopropylindenyl, fluorenyl, 4-methylfluorenyl, 2,7-di-tert-butylfluorenyl, tert-butylamido, cyclohexylamido, phenylamido, 2,6-diisopropylphenylamido, 2,6-di-tert-butylphenylamido, cyclododecylamido and —O.

14. An organometallic are selected from the group consisting of bis{[(tert-butylamido)dimethylsilyl)]cyclopentadienyl}zirconium, bis{[(tert-butylamido)diphenylsilyl)]cyclopentadienyl}zirconium, bis{[(tert-butylamido)phenylmethylsilyl)]cyclopentadienyl}zirconium, bis{[(tert-butylamido)ethylidene)]cyclopentadienyl}zirconium, bis{[(tert-butylamido)isopropylidene)]cyclopentadienyl}zirconium, bis{[(tert-butylamido)dimethylsilyl)]tetramethylcyclopenta-dienyl}zirconium, bis{[(tert-butylamido)dimethylsilyl)]methylcyclopentadienyl}zirconium, bis{[(2,6-diisopropylanilido)dimethylsilyl)]methylcyclopenta-dienyl}zirconium, bis{[(tert-butylamido)dimethylsilyl)]tert-butylcyclopenta-dienyl}zirconium, bis{[(tert-butylamido)dimethylsilyl)]indenyl}zirconium, bis{[(tert-butylamido)dimethylsilyl)]2-methylindenyl}zirconium, bis{[(tert-butylamido)dimethylsilyl)]2-methyl-4-phenylindenyl}zirconium, bis{[(tert-butylamido)dimethylsilyl)]2-methyl-4,5-benzoindenyl}zirconium, bis{[(tert-butylamido)dimethylsilyl)]2-methyl-4,6-diisopropylindenyl}zirconium, bis{[(tert-butylamido)dimethylsilyl)]fluorenyl}zirconium, bis{[(phenylamido)dimethylsilyl)]cyclopentadienyl}zirconium, bis{[(phenylamido)dimethylsilyl)]cyclopentadienyl}hafnium, bis{[(phenylamido)diphenylsilyl)]cyclopentadienyl}zirconium, bis{[(phenylamido)phenylmethylsilyl)]cyclopentadienyl}zirconium, bis{[(phenylamido)ethylidene)]cyclopentadienyl}zirconium, bis{[(phenylamido)isopropylidene)]cyclopentadienyl}zirconium, bis{[(phenylamido)dimethylsilyl)]tetramethylcyclopentadienyl}zirconium, bis{[(phenylamido)dimethylsilyl)]methylcyclopentadienyl}zirconium, bis{[(2,6-diisopropylanilido)dimethylsilyl)]methylcyclopentadienyl}zirconium, bis{[(phenylamido)dimethylsilyl)]tert-butylcyclopentadienyl}zirconium, bis{[(phenylamido)dimethylsilyl)]indenyl}zirconium, bis{[(phenylamido)dimethylsilyl)]2-methylindenyl}zirconium, bis{[(phenylamido)dimethylsilyl)]2-methyl-4-phenylindenyl}zirconium, bis{[(phenylamido)dimethylsilyl)]2-methyl-4,5-benzoindenyl}zirconium, bis{[(phenylamido)dimethylsilyl)]2-methyl-4,6-diisopropylindenyl}zirconium, bis{[(phenylamido)dimethylsilyl)]fluorenyl}zirconium, bis{[(2,6-diisopropylanilido)dimethylsilyl)]indenyl}zirconium, bis{[(2,6-diisopropylanilido)dimethylsilyl)]tert-butylcyclopentadienyl}zirconium, bis{[(2,6-di-tert-butylanilido)dimethylsilyl)]methylcyclopentadienyl}zirconium, bis{[(2,6-di-tert-butylanilido)dimethylsilyl)]indenyl}zirconium, bis(dimethylamido){[(cyclohexylanilido)dimethylsilyl)]-methylcyclopentandienyl}zirconium and bis{[(cyclohexylamido)dimethylsilyl)]indenyl}zirconium.

15. A catalyst component comprising at least one organometallic compound as claimed in claim 14 combined with at least one cocatalyst.

16. The catalyst as claimed in claim 15, wherein the cocatalyst is an aluminoxane having the formula V or VI

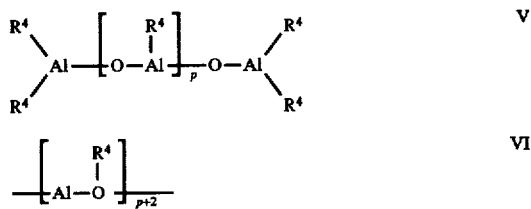

wherein the radicals $R^4$ are identical or different and each are a hydrocarbon radical having from 1 to 20 carbon atoms or hydrogen, and p is an integer from 2 to 50.

17. The catalyst as claimed in claim 15, wherein the cocatalyst is a compound of the formula $R^5_x NH_{4-x} BR^6_4$, $R^5_x PH_{4-x} BR^6_4$, $R^5_3 CBR^6_4$ or $BR^6_3$, and x is an integer from 1 to 4, and the radicals $R^5$ are identical or different and are each a saturated or unsaturated hydrocarbon radical having from 1 to 20 carbon atoms, wherein two of the radicals $R^5$ can form a saturated or unsaturated ring together with the atoms connected, the radicals $R^6$ are identical or different and each are an aromatic hydrocarbon radical having from 6 to 20 carbon atoms wherein the radical may be substituted by fluorine.

18. An organometallic compound of the formula I,

where

M is titanium, hafnium, vanadium, niobium, tantalum, scandium, yttrium or a rare earth metal, L are, independently of one another, identical or different and are each a π ligand, T are, independently of one another, identical or different and are each a bridge and A are independently of one another, identical or different and are each a π ligand or another electron donor.

19. An organometallic compound of the formula I,

where

M is a tetravalent metal,

L are, independently of one another, identical or different and are each a π ligand, T are, independently of one another, identical or different and are each a hydrocarbon bridge which optionally contains germanium and A are independently of one another, identical or different and are each a π ligand or another electron donor.

20. An organometallic compound of the formula I,

(I)

where M is a tetravalent metal, L are, independently of one another, identical or different and are each a π ligand, T are, independently of one another, identical or different and are each a bridge and A are independently of one another, identical or different and are each a π ligand, O, $PR^2$ or S wherein $R^2$ is hydrogen or a $C_1$–$C_{30}$ hydrocarbon radical.

21. The compound as claimed in claim 20, wherein A are independently of one another, identical or different and are each a π ligand.

* * * * *